United States Patent
Margus et al.

(10) Patent No.: US 7,335,474 B2
(45) Date of Patent: Feb. 26, 2008

(54) METHODS AND SYSTEMS FOR IDENTIFYING PREDISPOSITION TO THE PLACEBO EFFECT

(75) Inventors: Bradley Margus, Boca Raton, FL (US); David Cox, Belmont, CA (US); Jesse Hsu, Redwood City, CA (US)

(73) Assignee: Perlegen Sciences, Inc., Mountain View, CA (US)

( * ) Notice: Subject to any disclaimer, the term of this patent is extended or adjusted under 35 U.S.C. 154(b) by 338 days.

(21) Appl. No.: 10/940,410

(22) Filed: Sep. 13, 2004

(65) Prior Publication Data

US 2005/0079532 A1    Apr. 14, 2005

Related U.S. Application Data

(60) Provisional application No. 60/502,864, filed on Sep. 12, 2003.

(51) Int. Cl.
*C12Q 1/68* (2006.01)
(52) U.S. Cl. .......................................................... 435/6
(58) Field of Classification Search .................... None
See application file for complete search history.

(56) References Cited

U.S. PATENT DOCUMENTS

| | | | |
|---|---|---|---|
| 5,804,382 | A | 9/1998 | Sytkowski et al. |
| 5,851,763 | A | 12/1998 | Heym et al. |
| 6,040,138 | A | 3/2000 | Lockhart et al. |
| 6,132,965 | A | 10/2000 | Austin et al. |
| 6,219,964 | B1 | 4/2001 | Byrum et al. |
| 6,291,182 | B1 | 9/2001 | Schork et al. |
| 6,303,301 | B1 | 10/2001 | Mack |
| 6,479,238 | B1 | 11/2002 | Blumenfeld et al. |
| 6,673,908 | B1 | 1/2004 | Stanton, Jr. |
| 6,703,228 | B1 | 3/2004 | Landers et al. |
| 6,931,326 | B1 | 8/2005 | Judson et al. |
| 2004/0081996 | A1 | 4/2004 | Landers et al. |
| 2004/0082000 | A1 | 4/2004 | Stanton, Jr. |
| 2004/0115701 | A1 | 6/2004 | Cornings et al. |
| 2004/0171056 | A1 | 9/2004 | Stanton, Jr. |
| 2004/0229231 | A1 | 11/2004 | Frudakis et al. |

FOREIGN PATENT DOCUMENTS

| | | |
|---|---|---|
| WO | WO 97/10365 | 3/1997 |
| WO | WO 97/27317 | 7/1997 |
| WO | WO 98/56954 | 12/1998 |
| WO | WO 99/52942 | 10/1999 |
| WO | WO 00/18960 | 4/2000 |
| WO | WO 01/01218 A2 | 1/2001 |
| WO | WO 01/01218 A3 | 1/2001 |
| WO | WO 01/04270 | 1/2001 |
| WO | WO 02/27034 A2 | 4/2002 |
| WO | WO 02/27034 A3 | 4/2002 |

OTHER PUBLICATIONS

Fava, et al., The Problem of the Placebo Response in Clinical Trials for Psychiatric Disorders: Culprits, Possible Remedies, and a Novel Study Design Approach, Psychother Psychosom 2003:72:115-127.
Russo, The Biological Basis of the Placebo Effect, The Scientist, vol. 24, Dec. 9, 2002, pp. 30-31.
Altshuler et al., "Guilt by Association", Nature Genetics, Oct. 2000, 26:135.
Altshuler et al., "The Common PPARgammaPro12Ala Polymorphism is Associated with Decreased Risk of Type 2 Diabetes", Nature Genetics, Sep. 2000, 26:76.
Ardlie, K.G. et al., "Testing for Population Subdivision and Association in Four Case-Control Studies", Am. J. Hum. Genet., 2002, 71:304.
Bamshad et al., "Human Population Genetic Structure and Inference of Group Membership", Am. J. Hum. Genet., 2003, 73:578.
Barcellos et al., "Association Mapping of Disease Loci, by Use of a Pooled DNA Genomic Screen", Am. J. Hum. Genet., 1997, 61:734.
Cardon et al., "Association Study Designs for Complex Diseases", Nature Reviews / Genetics, 2001, 2:91.
Cargill, "Mining for SNPs: Putting the Common Variants—Common Disease Hypothesis to the Test", Pharmacogenomics, 2000, 1:27.
Chakravarti et al, "Population Genetics—Making Sense Out of Sequence", Nature Genetics Suppl., Jan. 1999, 21:56.
Cheng et al., "A Multilocus Genotyping Assay for Candidate Markers of Cardiovascular Disease Risk", Genome Research, 1999, 9:936.
Chizhikov et al., "Microarray Analysis of Microbial Virulence Factors", Applied and Environmental Microbiology, Jul. 2001, 67(7):3256.
Cho et al., "Bacterial Species Determination from DNA-DNA Hybridization by Using Genome Fragments and DNA Microarrays", Applied and Environmental Microbiology, Aug. 2001, 67(8):3677.
Collins et al., "Variation on a Theme: Cataloging Human DNA Sequence Variation", www.sciencemag.org, accessed on Jun. 27, 2002, 10 pgs.
Day et al., "Epidemiology & The Genetic Basis of Disease", Int'l. Journal of Epidemiology, 2001, 30:661.
Devlin et al., "Unbiased Methods for Population-Based Association Studies", Genetic Epidemiology, 2001, 21:273.
Devlin et al., "Genomic Control for Association Studies", Biometrics, 1999, 55:997.
Douglas et al., "Experimentally-Derived Haplotypes Substantially Increase the Efficiency of Linkage Disequilibrium Studies", Nature Genetics, Aug. 2001, 28:361.
Gray et al., "Single Nucleotide Polymorphisms as Tools in Human Genetics", Human Molecular Genetics, 2000, 9(16):2403.

(Continued)

*Primary Examiner*—James Martinell
(74) *Attorney, Agent, or Firm*—Deana A. Arnold; Gulshan H. Shaver, Esq.

(57) ABSTRACT

Methods and systems for identifying biological marker-placebo effect correlations are provided. Clinical trial design and data analysis of clinical trial data is modified to accommodate marker-placebo effect correlations.

13 Claims, 1 Drawing Sheet

OTHER PUBLICATIONS

Hacker et al., "Lack of Association Between an Interleukin-1 Receptor Antagonist Gene Polymorphism and Ulcerative Colitis", GUT, 1997, 40:623.

Hinde, "Evolution, Not Revolution", Trends in Biotechnology, 2000, 18:230.

Hinds et al., "Matching Strategies for Genetic Association Studies in Structured Populations", Am. J. Hum. Genet., 2004, 74:317.

Jorde, "Linkage Disequilibrium and the Search for Complex Disease Genes", Genome Research, 2000, 10:1435.

Judson et al., "The Predictive Power of Haplotypes in Clinical Response", Pharmacogenomics, 2000, 1:15.

Judson et al., "Notes from the SNPs vs. Haplotype Front", Pharmacogenomics, 2001, 2:7.

Kallioniemi, "Biochip Technologies in Cancer Research", Annals of Medicine, 2001, 33:142.

Kirk et al., "Single Nucleotide Polymorphism Seeking Long Term Association with Complex Disease", Nucleic Acids Research, 2002, 30:3295.

Kruglyak, "Prospects for Whole-Genome Linkage Disequilibrium Mapping of Common Disease Genes", Nature Genetics, Jun. 1999, 22:139.

Kruglyak et al., "Variation is the Spice of Life", Nature Genetics, Mar. 2001, 27:234.

Kwok, "Genetic Association by Whole-Genome Analysis?", Science, Nov. 23, 2001, 294:1669.

Lai, "Application of SNP Technologies in Medicine: Lessons Learned and Future Challenges", Genome Research, 2001, 11:927.

Lo et al., "Allelic Variation in Human Gene Expressions is Common in the Human Genome", Genome Research, 2003, 13:1855.

Lockhart et al., "Genomics, Gene Expression and DNA Arrays", Nature, Jun. 15, 2000, 405:827.

McCarthy et al., "The Use of Single-Nucleotide Polymorphism Maps in Pharmacogenomics", Nature Biotechnology, 2000, 18:505.

McKeigue et al., "Estimation of Admixture and Detection of Linkage in Admixed Populations by a Bayesian Approach: Application to African-American Populations", Annals of Human Genetics, 2000, 64:171.

Menzel, "Genetic and Molecular Analyses of Complex Metabolic Disorders: Genetic Linkage", Annals of the New York Academy of Sciences, 2002, 967:249-257.

Oestreicher, "4th Annual Pharmacogenomics and Medicine Lectures", Pharmacogenomics, 2001, 2:291.

Pennisi, "A Closer Look at SNPs Suggest Difficulties", Science, 1998, 281:1787.

Pritchard et al., "Use of Unlinked Genetic Markers to Detect Population Stratification in Association Studies", Am. J. Hum. Genet., 1999, 65:220.

Pritchard et al., "Inference of Population Structure Using Multilocus Genotype Data", Genetics, Jun. 2000, 155:945.

Reich et al., "Detecting Association in a Case-Control Study While Correcting for Population Stratification", Genetic Epidemiology, 2001(1):4.

Riley et al., "The Use of Single Nucleotide Polymorphisms in the Isolation of Common Disease Genes", Pharmacogenomics, 2000, 1:39.

Risch et al., "The Future of Genetic Studies of Complex Human Diseases", Science, 1996, 273:1516

Rosenberg et al., "Genetic Structure of Human Populations", Science, Dec. 20, 2002, 298:2381.

Roses, "Pharmacogenetics", Human Molecular Genetics, 2001, 10(20):2261.

Rothberg, "Mapping a Role for SNPs in Drug Development", Nature Biotechnology, 2001, 19:209.

Sham et al., "DNA Pooling: A Tool for Large-Scale Association Studies", Nature Reviews / Genetics, Nov. 2002, 3:862.

Strauss et al., "Microbial Pathogenesis: Genomics and Beyond", Science, May 2, 1997, 276:707.

Strohman, "Maneuvering in the Complex Path from Genotype to Phenotype", Science, Apr. 26, 2002, 296:701.

Templeton et al., "Cladistic Structure within the Human Lipoprotein Lipase Gene and its Implications for Phenotypic Association Studies", Genetics, Nov. 2000, 156:1259.

Uhl et al., "Polysubstance Abuse-Vulnerability Genes: Genome Scans for Association, Using 1,004 Subjects and 1,494 Single-Nucleotide Polymorphisms", Am. J. Hum. Genet., 2001, 69:1290.

Walter et al., "Prediction of Abacavir Resistance from Genotypic Data: Impact of Zidovudine and Lamivudine Resistance in Vitro and in Vivo", Antimicrobial Agents and Chemotherapy, Jan. 2002, 46(1):89.

Wayne et al., "Combining Mapping and Arraying : An Approach to Candidate Gene Identification", PNAS, Nov. 12, 2002, 99(23):14903.

Welford et al., "Detection of Differentially Expressed Genes in Primary Tumor Tissues Using Representational Differences Analysis Coupled to Microarray Hybridization", Nucleic Acids Research, 1998, 26(12):3059.

Yan et al., "Allelic Variation in Human Gene Expression", Science, Aug. 16, 2002, 297:1143.

Yang et al., "Combining SSH and cDNA Microarrays for Rapid Identification of Differentially Expressed Genes", Nucleic Acids Research, 1999, 27(6):1517.

Zee et al., "Multi-Locus Interactions Predict Risk for Post-PTCA Restenosis: An Approach to the Genetic Analysis of Common Complex Disease", The Pharmacogenomics Journal, 2002, 2:197.

Peterson, "Direct cDNA Selection", Chapter 3, vol. 2, Genome Analysis, A Laboratory Manual—Detecting Genes, Birren, Green, Klapholz, Myers, Roskams (Eds.), 1998, pp. 159-190.

METHODS AND SYSTEMS FOR IDENTIFYING PREDISPOSITION TO THE PLACEBO EFFECT

CROSS-REFERENCE TO RELATED APPLICATIONS

The present application claims priority to U.S. provisional patent application Ser. No. 60/502,864, filed Sep. 12, 2003, entitled "Methods and Systems for Identifying Predisposition to the Placebo Effect", the disclosure of which is specifically incorporated herein by reference in its entirety for all purposes.

BACKGROUND

The pharmaceutical industry spends billions of dollars every year in preclinical and clinical research in its quest for new therapeutics. A potential therapeutic must be assessed and approved for clinical efficacy and safety before it can be marketed. In cases where a drug entity is being evaluated for treatment of a condition where there is no conventional therapy available for treatment, the new drug is generally compared with a placebo. A placebo is a mixture lacking any active ingredients. Generally, the placebo is made to look similar to the "real" treatment. Clinical trials are structured to comprise a drug treatment group and a placebo treatment group. Typically, the clinical investigators and the subjects of the trial are blinded to the assignment of subjects in these groups.

It has been discovered that individuals receiving placebo treatments often experience an improvement in their condition, or alternatively, can experience side effects similar to those exhibited by individuals receiving drug treatment. Such a reaction to an "inert" treatment i.e. a treatment lacking an active ingredient is termed the "placebo effect". The placebo effect is common in medicine. It has been suggested that four out of ten people will feel some improvement as a result of taking a placebo. Theorists have attributed the placebo effect to have some sort of a psychological or physiological bases. However, it is likely that the physiological manifestation of the placebo effect is at least in some cases triggered by natural responses of the human body.

Some believe the placebo effect is psychological in nature, brought about by a belief in the treatment, or a perception with respect to a subjective feeling of improvement. For example, it has been postulated that the effectiveness of some drugs may be attributed almost entirely to the placebo effect. In one analysis of 19 clinical trials of antidepressants, the authors concluded that the expectation of improvement, not adjustments in brain chemistry, accounted for 75 percent of the drugs' effectiveness (Kirsch et al. (1998) "Listening to Prozac but Hearing Placebo: A Meta-Analysis of Antidepressant Medication" *Prevention & Treatment*, Volume 1, Article 0002a. In an earlier study, Sapirstein analyzed 39 studies, done between 1974 and 1995, of depressed patients treated with drugs, psychotherapy, or a combination of both. He found that 50 percent of the drug effect is due to the placebo response.

The placebo effect has also been used as an explanation for the apparent benefits of certain complementary therapies where patients are sure they feel better after having therapy, even where there is no scientific evidence that the therapy has any effect on their illness.

It would be useful to understand cause(s) of the placebo effect and to predict their occurrence before including a given individual in a clinical trial. Understanding and/or being able to predict placebo effects could help in filtering out noise in clinical trials and in avoiding flawed study designs. It would be a significant benefit to the pharmaceutical industry if one could simply avoid or reduce the impact of the placebo effect on the data derived from a clinical trial.

SUMMARY

The present invention provides methods and systems for identifying underlying biological (e.g., genetic, epigenetic or environmental) bases for placebo effects, as well as related systems. The invention also provides methods and systems for using such information in designing clinical trials, in drug screening and the like.

Accordingly, in a first aspect, the invention provides methods of identifying a biological basis for a placebo effect. In the methods, at least a first biological marker of a first individual or population of individuals is compared to the first biological marker, or to a second biological marker, for a second individual or population of individuals. For example, the marker can be a single marker that is assessed for expression characteristics (an expression marker), a protein marker, or a marker for one or more alleles at one or more genetic loci. Alternately, multiple markers can be identified simultaneously and assessed in the two individuals or populations to identify patterns of loci or expression markers that are relevant. In any case, the first or second marker is correlated to the placebo effect at issue, thereby identifying a genetic basis for the placebo effect.

Any of a variety of placebo effects can be tested for, including improvements in a condition or conditions of the first or second individual or population in response to administration of the placebo, and/or a deterioration in a condition of the first or second individual or population in response to administration of the placebo. Placebo effects can also include, e.g., unwanted side effects, e.g., similar to those that may be encountered upon administration of a given drug (e.g., headache, stomach upset, sexual side effects, sleep pattern alterations, diarrhea, etc.). The placebo itself can be any of those typically administered to patient, e.g., tablets, suspensions or injections of inert ingredients, e.g., sugar pills or starch pills, or other mock therapies, e.g., fake surgeries, fake psychiatric care, or others that have been used, typically as controls, for a putative "real" treatments. Thus, the placebo can comprise one or more inert ingredients, or even one or more active ingredients (e.g., where the activity is expected to be orthogonal to the therapy at issue).

The biological markers that are screened for correlation to the placebo effect can be any of those types of markers that can be screened for, e.g., genetic markers such as allelic variants of a genetic locus (e.g., as in single nucleotide polymorphisms, or "SNPs"), expression markers (e.g., presence or quantity of mRNAs and/or proteins), and/or the like. Examples of markers include polymorphisms, single nucleotide polymorphisms, presence of one or more nucleic acids in a sample, absence of one or more nucleic acids in a sample, presence of one or more genomic DNA sequences, absence or one or more genomic DNA sequences, presence of one or more mRNA sequences, absence of one or more mRNA sequences, expression levels of one or more mRNAs, presence of one or more proteins, expression levels of one or more proteins, and/or data derived from any of the preceding or combinations thereof. Essentially any number of markers can be detected, using available methods, e.g., using array technologies that provide high density, high throughput marker mapping, PCR based techniques, mass spectrometry techniques, and others. Thus, at least about 1, 10, 100, 1,000, 10,000, or even 100,000 or more genetic markers can be tested, simultaneously or in a serial fashion (or combination thereof), for correlation to a placebo effect, in the first and/or second population. Combinations of markers can also be desirably tested, e.g., to identify genetic or expression patterns in populations that are correlated to the placebo effect. For example, comparing the first and second genetic marker can include determining a first haplotype for the first individual or population and determining a second haplotype of the second individual or population, and comparing the first and second haplotypes to identify correlations with one or more placebo effects.

The biological marker to be detected can be any detectable biological component, whether inherited, due to environmental effects or both. Commonly detected markers include genetic markers (e.g., DNA sequence markers present in genomic DNA or expression products thereof) and expression markers (which can reflect genetically coded factors, environmental factors, or both). Where the markers are expression markers, the methods can include determining a first expression profile for the first individual or population (e.g., of one or more expressed markers, e.g., a set of expressed markers) and comparing the first expression profile to a second expression profile for the second individual or population. In this example, correlating the first or second marker can include correlating the first or second expression profile to the placebo effect.

Correlation of the first or second marker to the placebo effect optionally includes performing one or more statistical tests for correlation. Many statistical tests are known, and most are computer-implemented for ease of analysis.

In a second related set of embodiments, methods of screening an individual or population for susceptibility to a placebo effect are provided. In these methods, a biological sample derived from the individual or population, or data corresponding to the biological sample is analyzed for a presence or absence of one or more biological marker(s) associated with the placebo effect, whereby a susceptibility to the placebo effect is determined. Thus, the embodiments noted above provide, e.g., methods of determining whether an association between a marker and a placebo effect exist, while this set of embodiments provides, e.g., a method of screening individuals for a placebo effect correlation with a marker, once such a correlation is determined (e.g., by any method noted above, or any other method). It will be appreciated that the types of markers, types of placebo effects, and types of placebos that are applicable to this method are those noted above.

Most typically, this class of embodiments will include determining the presence or absence of the biological marker in the biological sample (or in data corresponding to the biological sample). For example, the method optionally includes obtaining the biological sample and testing the sample for a genetic or other biological marker.

As will be discussed in more detail herein, the identification of a marker within a biological sample, from a patient, that shows a correlation to a placebo effect can be useful in designing clinical trials or to detect other experimental drug effects in populations, by accounting for the placebo effect in the relevant clinical trial or experiment. However, the method also provides an avenue for therapy. For example, those members of a population that display a placebo effect provides an avenue for treatment of such members, i.e., by administering placebo to the members of the population that show a placebo effect.

The invention further provides for the design of clinical or other trials to account for the placebo effect, taking biological predispositions to the placebo effect into account. Thus, in a first embodiment of this approach, methods of testing a placebo-normalized activity of a putative therapeutic agent are provided. In the methods, the putative therapeutic agent is administered to a first patient population comprising one or more patients. A desired activity of the therapeutic agent is detected. Members that are genetically predisposed to display a placebo effect are identified in the population. Based upon this identification, activity data from the detecting step is normalized to account for the placebo effect, thereby determining the placebo-normalized activity of the putative therapeutic agent.

In a related class of embodiments, alternate methods of testing a placebo-normalized activity of a putative therapeutic agent are provided. In these related methods, members of a first patient population that are genetically predisposed to display a placebo effect are identified. The members are selected (for or against) to provide a placebo-effect normalized patient population. The putative therapeutic agent is administered to the placebo-effect normalized patient population, and, a desired activity of the putative therapeutic agent in the placebo-effect normalized patient population is detected (thereby determining a placebo-normalized activity of the putative therapeutic agent).

In either of these related aspects of the invention, identifying members of the first patient population typically includes identifying at least one biological (e.g., genetic) marker in members of the first population that is correlated to the placebo effect. The types of markers to be detected and the types of placebo effects to be accounted for include any of those noted above.

Normalizing activity data optionally includes revising estimates of a correlation between the desired activity and administration of the putative therapeutic agent, based upon an expected placebo effect on this correlation. That is, the expected placebo effect normalization takes into account the effect on the population members that are genetically predisposed to display the placebo effect. Such normalizing is optionally performed after obtaining a complete desired activity data set corresponding to the desired activity of the therapeutic agent in the first population, or can be performed during a process of obtaining a desired activity data set corresponding to the desired activity of the therapeutic agent in the first population.

In addition to the use of placebo effect correlations to design clinical and other experimental trials, the correlations can be used to identify placebo effect-modulatory agents (which can suppress or enhance placebo effects). Such agents can be desirable e.g., as an adjunct to clinical trial design to reduce placebo effects, or as a form of therapy, to enhance the placebo effect as a form of treatment. The methods include, e.g., administering one or more putative placebo effect-modulatory agent to an individual that displays a placebo effect, and determining whether the putative placebo effect-modulatory agent modulates the placebo effect in the individual. This, in turn, determines whether the putative placebo effect-modulatory agent is an actual placebo effect-modulatory agent.

The placebo effect-modulatory agent is optionally a placebo itself, but can also be a therapeutic drug that has an ordinary biological effect. In any case, the actual placebo effect-modulatory agent modulates an activity of a placebo administered to the individual, thereby modulating the placebo effect.

In addition to the above methods, the invention provides related systems for practicing the methods (and systems with different functionality as well). In a first class of system embodiments, systems for correlating biological marker data to a biologically-encoded placebo effect are provided. The system includes at least one genetic marker data set corresponding to at least one genetic marker that correlates with at least one placebo effect. The system also typically includes computer-implemented system instructions for correlating the data set to the placebo effect.

For example, the system can include a look up table corresponding to one or more placebo effect genetic susceptibility marker, where the computer implemented system instructions compare the genetic marker data set to the look up table to determine whether the at least one genetic marker correlates with one or more entry in the look up table.

Similarly, systems for screening an individual or population for susceptibility to a placebo effect are provided. The systems include, e.g., data corresponding to one or more test genetic markers in a biological sample derived from an individual or population and a look up table corresponding to one or more susceptibility markers. Computer-implemented system instructions compare the test genetic markers to the susceptibility markers, thereby determining whether the individuals comprise one or more test genetic marker associated with the placebo effect.

Optionally, the above systems can include a selection module that selects for or against the individual or population based upon whether the individual comprises the one or more susceptibility markers. Similarly, the systems can include a data normalization module that comprises system instructions that normalize one or more activity data sets for the placebo effect.

In an additional aspect, the invention provides a system for determining a placebo-normalized activity of a putative therapeutic agent. The system includes activity data corresponding to a desired activity of a putative therapeutic agent in a first patient population comprising one or more patients and placebo effect data corresponding to population members of the first population that are genetically predisposed to display a placebo effect. Computer-implemented system instructions provide a normalized data set by adding or subtracting values from the activity data, based upon the placebo effect data.

In yet an additional system embodiment, systems for identifying a genetic basis for a placebo effect are provided. The systems include at least one genetic marker data set corresponding to at least a first genetic marker and the first or a second genetic marker for a second individual or population of individuals. Computer-implemented system instructions compare the marker(s) for the individuals and correlate them to the placebo effect, thereby identifying a genetic basis for the placebo effect.

Any of the above systems optionally include additional system components for interfacing with a user. For example, the systems can include a user viewable display for viewing an output of the computer-implemented system instructions, user input devices (e.g., keyboards or pointing devices such as a mouse) for inputting user commands and activating the system, etc. Typically, the system of interest includes a computer, wherein the various computer-implemented system instructions are embodied in computer software, e.g., stored on computer readable media.

Any of the above systems can include a data acquisition module for detecting one or more detectable genetic marker (e.g., one or more array comprising one or more biomolecular probes, detectors, fluid handlers, or the like). The biomolecular probes of such a data acquisition module can include any that are appropriate for detecting the biological marker, e.g., oligonucleotide probes, proteins aptamers, antibodies, etc.

Any of the above systems can be packaged as kits, e.g., comprising one or more system components and instructional materials for practicing one or more of the methods herein, packaging materials, or the like.

BRIEF DESCRIPTION OF THE DRAWINGS

FIG. 1 illustrates a schematic of the method for performing an association study between cases and controls for a given phenotype.

DETAILED DESCRIPTION OF THE INVENTION

Figure 1:
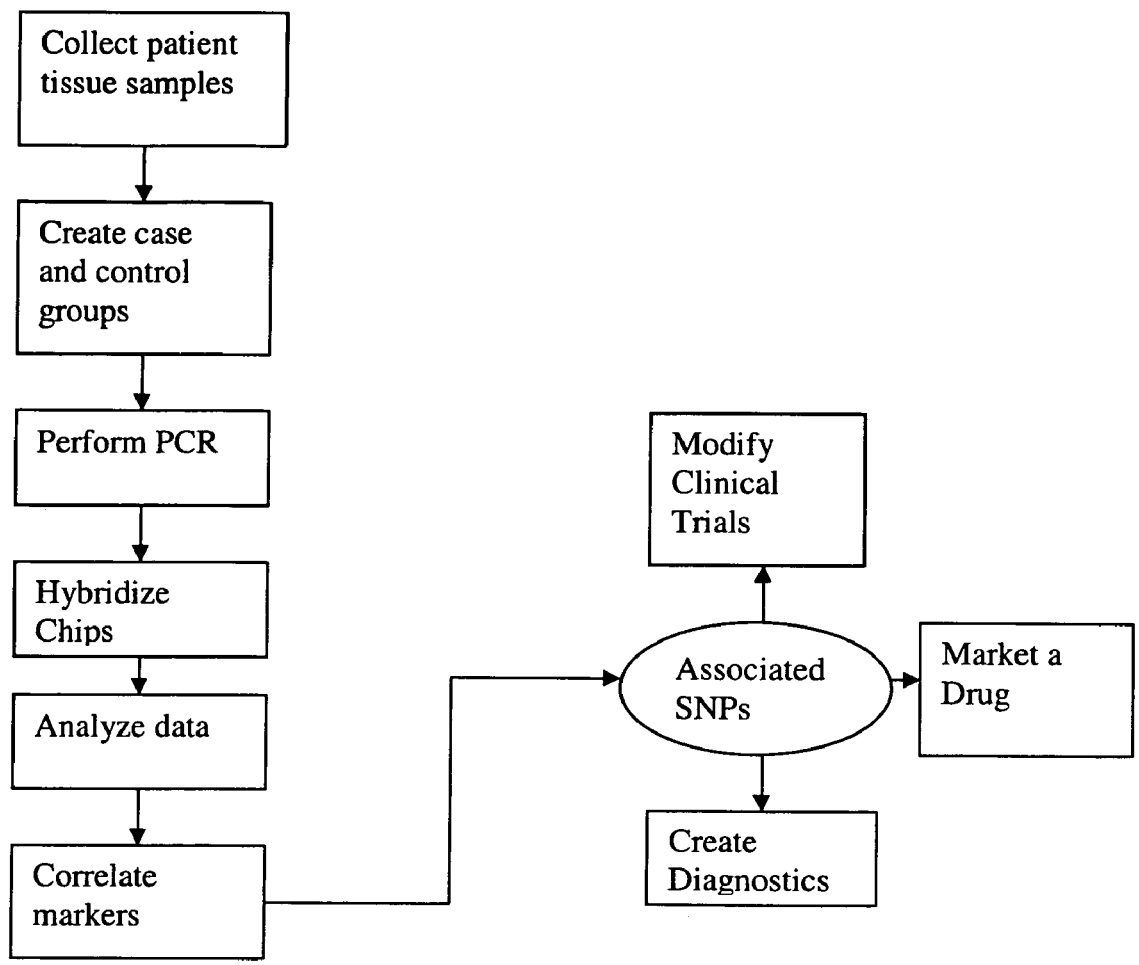
FIG. 1.

The present application is directed to methods and systems for identifying genetic and other biological bases of placebo effects. It is well recognized that placebo effects have both positive and negative impacts on modern science and pharmacology.

In general, clinicians can be frustrated by the placebo effect in their efforts to analyze therapies, because, quite frequently, a drug clinical trial will result in unsatisfactory results for the drug entity under evaluation in a standard double-blinded test against a placebo. This is because the placebo effect is strong enough that the drug being tested is not significantly better than the placebo in treating a particular condition or phenotype. The methods of the present invention provide mechanisms for identifying a person's predisposition to a placebo effect, which makes it possible to improve the sensitivity and accuracy of clinical trial testing. For example, the methods provide mechanisms for screening a nucleic acid sample of an individual (e.g., derived from genomic DNA, or expressed nucleic acids such as mRNA) to determine if the individual has susceptibility or a predisposition to exhibiting a placebo effect, thereby biasing observed data in a clinical trial setting.

Definitions

Before describing the present invention in detail, it is to be understood that this invention is not limited to particular systems or methods, which can, of course, vary. It is also to be understood that the terminology used herein is for the purpose of describing particular embodiments only, and is not intended to be limiting. As used in this specification and the appended claims, the singular forms "a", "an" and "the" include plural referents unless the context clearly dictates otherwise. Thus, for example, reference to "a substrate" optionally includes a combinations of two or more substrates; reference to an "RNA" optionally includes a plurality of RNAs, and/or the like.

The "placebo effect" is a measurable, observable, or perceived improvement in health not attributable to a treatment.

A "biological marker" is a detectable biological molecule that is present in a biological sample. These include "genetic markers" which are any heritable biological molecules (e.g., genomic DNA, mitochondrial DNA, etc.) or partial or complete nucleic acid copies thereof (RNAs, mRNAs, cDNAs, etc.). "Expression markers," are molecules that are produced by a process that includes expression (transcription and/or translation) of heritable biological material (e.g., RNAs, mRNAs, proteins, etc.), or products of such molecules (cDNAs, molecules made by biosynthesis provided in whole or in part by such molecules (e.g., lipids, hormones, etc.)). Expression markers can be tested for presence or absence of the marker or can be quantified in a system of interest.

A "biological basis" is an underlying biological reason for an observed or observable event. The reason can have genetic or environmental components, or both. A "genetic basis" is a heritable biological basis. An "environmental basis" is a reason for an observed or observable event that is caused by an environmental input on a system of interest. Thus, a biological basis can be genetic, or can have both genetic and environmental causes.

A marker is "correlated" with a placebo effect when it can be statistically linked (positively or negatively) to the placebo effect. This correlation is often inferred as causal in nature, but it need not be.

A "haplotype" is a set of genetic loci found in the heritable material of an individual or population. It can be a contiguous or non-contiguous set of such loci.

A nucleic acid is "amplified" when one or more copies of the nucleic acid, or at least one strand thereof, are copied and/or transcribed. Thus, a DNA can be amplified to produce DNAs or RNAs, and RNA can be amplified by transcribing it from DNA (which, itself, can be made by reverse transcription of an RNA), etc.

An "amplicon" is a molecule made by copying or transcribing another molecule, e.g., as occurs in PCR, transcription, and/or cloning.

A "translation product" is a product (typically a polypeptide) produced as a result of the translation of a nucleic acid. A "transcription product" is a product (e.g., RNA, optionally including mRNA, or, e.g., a catalytic or biologically active RNA) produced as a result of transcription of a nucleic acid.

An "array" is an assemblage of elements. The assemblage can be spatially ordered (a "patterned array") or disordered (a "randomly patterned" array). The array can form or comprise one or more functional elements (e.g., a probe region on a microarray) or it can be non-functional.

As used herein, the term "SNP" or "single nucleotide polymorphism" refers to a genetic variation between individuals; e.g., a single nitrogenous base position in the DNA of organisms that is variable. As used herein, "SNPs" is the plural of SNP. Of course, when one refers to DNA herein such reference may include derivatives of DNA such as amplicons, RNA transcripts, etc.

Methods

The invention provides several different interrelated methods for correlating biological markers and the placebo effect, and in using such correlation information once identified. For example, the invention provides methods of identifying biological (e.g., genetic or expression) markers that correlate with a placebo effect. Once any such correlation is identified, whether by the methods of the invention or otherwise, the invention provides methods for identifying individuals or populations that are susceptible to the placebo effect. Once such individuals or populations are identified, the methods of the invention can include normalizing experimental data to take account of the susceptibility to the placebo effect, or the populations in experiments can be biased to account for the susceptibility, or both. Similarly, the identification of susceptibility can be used to provide effective therapeutic treatments to susceptible individuals, using placebo therapy. Finally, methods of screening for modulators of the placebo effect, in susceptible or non-susceptible individuals are also provided.

Correlating Biological Markers to Placebo Effect Susceptibility

As noted, the invention provides methods of identifying a biological basis for a placebo effect. In the methods, at least a first biological marker (e.g., a polymorphism, mRNA marker, or the like) of a first individual or population of individuals is compared to one or more markers in a second individual or population of individuals (or additional individuals or populations—a few or many individuals or populations can be simultaneously or serially screened in this method). The individual or population will most commonly be a human individual (e.g., a patient) or population of human patients. The comparison can be done on the same marker between the two patients or populations (or, related, e.g., allelic forms thereof), or between different markers, or between combinations of markers for the patients or populations selected for comparison. For example, the marker can be a single marker that is assessed for expression characteristics (an expression marker), or a marker for one or more alleles at one or more loci, or can be multiple markers (including haplotypes and/or genotypes). In the case of multiple markers these can be identified serially or simultaneously and assessed in the two or more individuals or populations, to identify patterns of loci or expression markers that are relevant. In any case, the marker or markers are correlated to the placebo effect at issue, thereby identifying a genetic basis for the placebo effect.

Screening Biological Markers to Identify Markers for Placebo Effect Susceptibility Biological markers can be identified/screened by any available marker detection method. The precise method of performing marker detection/screening can vary depending on the marker to be tested (e.g., whether the marker is a nucleic acid or protein, or other molecule), and/or based upon the screening platform chosen by one of skill. For example, where the marker(s) is/are a nucleic acid or nucleic acids, the marker(s) can be screened by any available hybridization methods (Southern blotting, northern blotting, southwestern blotting, northwestern blotting, array-based detection, etc.), real time amplification methods (e.g., Taq-Man™ or molecular beacon mediated methods), reporter system methods (e.g., via complementation or linked expression of reporter moieties, e.g., as in a two-hybrid system), or the like. Array-based methods are one preferred method of detecting nucleic acid markers, particularly where many markers are to be detected simultaneously. Similarly, where the marker(s) is/are a protein or proteins, common detection methods include antibody-based detection (e.g., ELISA, western blotting, antibody or ligand arrays, etc.) proteomic methods (e.g., mass-spectrometry, SPIR, etc.).

Methods of detecting markers by such technologies are well known. For example, standard hybridization-based detection methods such as Southern and Northern blotting are found in Sambrook et al. (2001) *Molecular Cloning, A Laboratory Manual* 3rd Edition Cold Spring Harbor Laboratory, ISBN: 0879695773 ("Sambrook") and Ausubel et al., eds., *Current Protocols*, a joint venture between Greene Publishing Associates, Inc. and John Wiley & Sons, Inc., (supplemented through 2003) ("Ausubel"). An overview of basic hybridization procedures can be found in Tijssen (1993) *Laboratory Techniques in Biochemistry and Molecular Biology—Hybridization with Nucleic Acid Probes*, e.g., part I chapter 2, "Overview of principles of hybridization and the strategy of nucleic acid probe assays," (Elsevier, N.Y.), as well as in Ausubel, supra. Hames and Higgins (1995) *Gene Probes* 1 IRL Press at Oxford University Press, Oxford, England, (Hames and Higgins 1) and Hames and Higgins (1995) *Gene Probes* 2 IRL Press at Oxford University Press, Oxford, England (Hames and Higgins 2) provide details on the synthesis, labeling, detection and quantification of DNA and RNA, including probes.

Array-Based Detection

Array-based detection can be performed using commercially available arrays, e.g., from Affymetrix (Santa Clara, Calif.) or other manufacturers. Reviews regarding the operation of nucleic acid arrays include Sapolsky et al. (1999) "High-throughput polymorphism screening and genotyping with high-density oligonucleotide arrays." *Genetic Analysis: Biomolecular Engineering* 14:187-192; Lockhart (1998) "Mutant yeast on drugs" *Nature Medicine* 4:1235-1236; Fodor (1997) "Genes, Chips and the Human Genome." *FASEB Journal* 11:A879; Fodor (1997) "Massively Parallel Genomics." *Science* 277:393-395; and Chee et al. (1996) "Accessing Genetic Information with High-Density DNA Arrays." *Science* 274:610-614. Array based detection is particularly preferred for identification of placebo effect susceptibility markers, due to the inherently high-throughput nature of array based detection.

A variety of probe arrays have been described in the literature and can be used in the context of the present invention for detection of markers that can be correlated to placebo effect susceptibility. For example, DNA probe array chips or larger DNA probe array wafers (from which individual chips would otherwise be obtained by breaking up the wafer) are used in one embodiment of the invention. DNA probe array wafers generally comprise glass wafers on which high density arrays of DNA probes (short segments of DNA) have been placed. Each of these wafers can hold, for example, approximately 60 million DNA probes that are used to recognize longer sample DNA sequences (e.g., from individuals or populations, e.g., that comprise markers of interest). The recognition of sample DNA by the set of DNA probes on the glass wafer takes place through DNA hybridization. When a DNA sample hybridizes with an array of DNA probes, the sample binds to those probes that are complementary to the sample DNA sequence. By evaluating to which probes the sample DNA for an individual hybridizes more strongly, it is possible to determine whether a known sequence of nucleic acid is present or not in the sample, thereby determining whether a marker found in the nucleic acid is present.

The use of DNA probe arrays to obtain marker information typically involves the following general steps: design and manufacture of DNA probe array wafers, preparation of the sample, hybridization of target DNA to the array, detection of hybridization events and data analysis to determine sequence. Preferred wafers are manufactured using a process adapted from semiconductor manufacturing to achieve cost effectiveness and high quality, and are available from Affymetrix, Inc of Santa Clara, Calif.

For example, probe arrays can be manufactured by light-directed chemical synthesis process, which combines solid-phase chemical synthesis with photolithographic fabrication techniques as employed in the semiconductor industry. Using a series of photolithographic masks to define chip exposure sites, followed by specific chemical synthesis steps, the process constructs high-density arrays of oligonucleotides, with each probe in a predefined position in the array. Multiple probe arrays can be synthesized simultaneously on a large glass wafer. This parallel process enhances reproducibility and helps achieve economies of scale.

Once fabricated, DNA probe arrays can be used to obtain data regarding presence and expression levels for markers of interest. The DNA samples are tagged with a fluorescent reporter group by standard biochemical methods. The labeled samples are incubated with a wafer, and segments of the samples bind, or hybridize, with complementary sequences on the wafer. The wafer is then scanned and the patterns of hybridization are detected by emission of light from the fluorescent reporter groups. Because the identity and position of each probe on the wafer is known, the nature of the DNA sequences in the sample applied to the wafer can be determined. When these arrays are used for genotyping experiments, they may be referred to as genotyping arrays.

Once fabricated, the arrays are ready for hybridization. The nucleic acid sample to be analyzed is isolated, amplified and, typically, labeled with a fluorescent reporter group. The labeled nucleic acid sample is then incubated with the array using a fluidics station and hybridization oven. After the hybridization reaction is complete, the array is inserted into a scanner, where patterns of hybridization are detected. The hybridization data are collected as light is emitted from the fluorescent reporter groups already incorporated into the labeled nucleic acid, which is now bound to the probe array. Probes that most clearly match the labeled nucleic acid produce stronger signals than those that have mismatches. Since the sequence and position of each probe on the array are known, by complementarity, the identity of the nucleic acid sample applied to the probe array can be identified.

In one embodiment, the DNA sample for an individual is differentially labeled and hybridized with a single set of the designed genotyping arrays. In this way two sets of data can be obtained from the same physical arrays. Labels that can be used include, but are not limited to, cychrome, fluorescein, or biotin (later stained with phycoerythrin-streptavidin after hybridization). Two-color labeling is described in U.S. Pat. No. 6,342,355, incorporated herein by reference in its entirety. Each array may be scanned such that the signal from both labels is detected simultaneously, or may be scanned twice to detect each signal separately. It has been found that measured intensities for cychrome and fluorescein labeled samples can have a non-linear relationship. One origin of this effect is believed to be owing to the saturation of sample molecules with cychrome. Without wishing to be bound by theory, it is believed that adjacent cychrome on the surface of the labeled molecules may interfere and reduce the amount of light emitted. Therefore, in one embodiment, only a single staining step is used for cychrome, rather than two stains. Alternatively, a reduced amount of cychrome effective to reduce the non-linearity in detected intensity can be used in the staining.

Intensity data is collected by the scanner for all the markers for each of the individuals that are tested for presence of the marker. The measured intensities are a measure indicative of the amount of a particular marker present in the sample for a given individual. The intensity data is then processed to provide corresponding marker information for the various intensities.

Detecting Markers in Solution Phase Assays

An additional common approach to marker detection includes various real time amplification detection methods, e.g., utilizing molecular beacons or TaqMan™ probes, detection of intercalating dyes, detection of labels incorporated into the amplification probes or the amplified nucleic acids themselves, e.g., following electrophoretic separation of the amplification products from unincorporated label), hybridization based assays (e.g., array based assays) and/or detection of secondary reagents that bind to the nucleic acids. Details on these general approaches is found in the references cited herein, e.g., Sambrook, Ausubel, and the references in the sections below. Additional labeling strategies for labeling nucleic acids and corresponding detection strategies can be found, e.g., in Haugland (2003) *Handbook of Fluorescent Probes and Research Chemicals Ninth Edition* by Molecular Probes, Inc. (Eugene Oreg.) (Also available on CD ROM).

Amplicons of nucleic acids that incorporate or otherwise correspond to markers of interest can be detected in a solution phase, eliminating any need for size/charge separation and/or hybridization or sequencing (although these approaches can be used, if desired, to provide additional information of what sequences are being detected), for a number of applications. This is particularly useful in the context of the present invention for the detection of placebo effect susceptibility markers after a correlation is made, to identify individuals or populations that display susceptibility (discussed in more detail below). That is, solution phase marker detection is generally lower throughput than is array based detection. Thus, it is most easily used to identify smaller sets of placebo effect susceptibility markers, e.g., once correlations have already been established. However, solution phase assays can also be used for screening to identify markers, though array based approaches are preferred due to their higher throughput.

In any case, any of a variety of solution phase assays can be used. For example, the amount of a double-stranded DNA amplicon can be determined by monitoring double-strand DNA specific dye incorporation by the amplicon. Similarly, direct detection of RNA products can be practiced by monitoring dye-specific incorporation of RNA Dyes. TaqMan™ or molecular beacon-mediated approaches can be used.

Detection with Specific Dyes

In one aspect of the invention, nucleic acid markers are detected in a solution phase assay via detection with specific dyes. These can include detection of RNA amplicons corresponding to markers, e.g., where RNA amplification methods are used for marker detection, or detection of DNA amplicons where DNA amplification methods are used for marker selection/identification. For example, a number of RNA specific dyes are available, such as RiboGreen®. This dye is an example of an ultrasensitive fluorescent nucleic acid stain for quantifying RNA in solution and is available from Molecular Probes (catalogue No. R-11491 and R-11490). Similarly, the PicoGreen dye is a double-stranded DNA-specific dye (available, e.g., from Molecular Probes) that can be used to monitor and quantify double stranded DNA amplicons. See, e.g., Haugland (2003). For example, Molecular Probes, Chapter 8 provides details regarding quantification of DNA in solution. For detecting ssDNA amplicons in solution, the OliGreen ssDNA quantification reagent from Molecular Probes (No. O-7582) and/or (No. O-11492) can be used). Other dyes such as the Cyanine Dyes and Phenanthridine Dyes can also be used for nucleic acid quantification in solution and are, therefore, adaptable to use in the present invention. See, Haughland (2003), Supra, for a discussion of these and many other nucleic acid staining and quantification dyes.

Detection of Protein Expression Products

Proteins are encoded by nucleic acids, including those comprising markers that are correlated to placebo effects. For a description of the basic paradigm of molecular biology, including the expression (transcription and/or translation) of DNA into RNA into protein, see, Alberts et al. (2002) *Molecular Biology of the Cell.* $4^{th}$ *Edition* Taylor and Francis, Inc., ISBN: 0815332181 ("Alberts"), and Lodish et al. (1999) *Molecular Cell Biology,* $4^{th}$ *Edition* W H Freeman & Co, ISBN: 071673706X ("Lodish"). Accordingly, proteins can be detected as markers, e.g., by detecting different protein isotypes between individuals or populations, or by detecting a differential presence, absence or expression level of a protein of interest.

A variety of protein detection methods are known and can be used to distinguish markers. In addition to the various references noted supra, a variety of protein manipulation and detection methods are well known in the art, including, e.g., those set forth in R. Scopes, *Protein Purification,* Springer-Verlag, N.Y. (1982); Deutscher, *Methods in Enzymology Vol. 182: Guide to Protein Purification,* Academic Press, Inc. N.Y. (1990); Sandana (1997) *Bioseparation of Proteins,* Academic Press, Inc.; Bollag et al. (1996) *Protein Methods,* $2^{nd}$ *Edition* Wiley-Liss, NY; Walker (1996) *The Protein Protocols Handbook* Humana Press, NJ, Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice* $3^{rd}$ *Edition* Springer Verlag, NY; Janson and Ryden (1998) *Protein Purification: Principles. High Resolution Methods and Applications. Second Edition* Wiley-VCH, NY; and Walker (1998) *Protein Protocols on CD-ROM* Humana Press, NJ; and the references cited therein. Additional details regarding protein purification and detection methods can be found in Satinder Ahuja ed., *Handbook of Bioseparations,* Academic Press (2000).

"Proteomic" detection methods, which detect many proteins simultaneously have been described. These can include various multidimensional electrophoresis methods (e.g., 2-d gel electrophoresis), mass spectrometry based methods (e.g., SELDI, MALDI, electrospray, etc.), or surface plasmon resonance methods. For example, in MALDI, a sample is usually mixed with an appropriate matrix, placed on the surface of a probe and examined by laser desorption/ionization. The technique of MALDI is well known in the art. See, e.g., U.S. Pat. No. 5,045,694 (Beavis et al.), U.S. Pat. No. 5,202,561 (Gleissmann et al.), and U.S. Pat. No. 6,111,251 (Hillenkamp). Similarly, for SELDI, a first aliquot is contacted with a solid support-bound (e.g., substrate-bound) adsorbent. A substrate is typically a probe (e.g., a biochip) that can be positioned in an interrogatable relationship with a gas phase ion spectrometer. SELDI is also a well known technique, and has been applied to diagnostic proteomics. See, e.g. Issaq et al. (2003) "SELDI-TOF MS for Diagnostic Proteomics" *Analytical Chemistry* 75:149A-155A.

Types of Markers to be Screened For

The biological markers that are screened for correlation to the placebo effect can be any of those types of markers that can be screened for, e.g., genetic markers such as allelic variants of a genetic locus (e.g., as in single nucleotide polymorphisms, or "SNPs"), expression markers (e.g., presence or quantity of mRNAs and/or proteins), and/or the like.

The nucleic acid of interest to be amplified, transcribed, translated and/or detected in the methods of the invention can be essentially any nucleic acid, though nucleic acids derived from human sources are especially relevant to the detection of markers associated with placebo effect susceptibility. The sequences for many nucleic acids and amino acids (from which nucleic acid sequences can be derived via reverse translation) are available. No attempt is made to identify the millions of known nucleic acids, any of which can be detected in the methods of the invention. Common sequence repositories for known nucleic acids include GenBank® EMBL, DDBJ and the NCBI. Other repositories can easily be identified by searching the internet. The nucleic acid to be amplified, transcribed, translated and/or detected can be an RNA (e.g., where amplification includes RT-PCR or LCR, the Van-Gelder Eberwine reaction or Ribo-SPIA) or DNA (e.g., amplified DNA, cDNA or genomic DNA), or even any analogue thereof (e.g., for detection of synthetic nucleic acids or analogues thereof, where the sample of interest includes artificial nucleic acids). Any variation in a nucleic acid between individuals or populations can be detected as a marker for placebo effect susceptibility, e.g., a mutation, a polymorphism, a single nucleotide polymorphism (SNP), an allele, an isotype, etc. Further, one can detect variation in expression levels or gene copy numbers as biological markers of placebo effect susceptibility.

For example, the methods of the invention are useful in screening samples obtained or derived from patients for a placebo effect susceptibility marker nucleic acid of interest, e.g., from bodily fluids (blood, urine etc.), tissue, and/or waste from the patient. Thus, stool, sputum, saliva, blood, lymph, tears, sweat, urine, vaginal secretions, ejaculatory fluid or the like can easily be screened for nucleic acids by the methods of the invention, as can essentially any tissue of interest. These samples are typically obtained, following informed consent, from a patient by standard medical laboratory methods.

Prior to amplification and/or detection of a nucleic acid comprising a marker, the nucleic acid is optionally purified from the samples by any available method, e.g., those taught in Berger and Kimmel, *Guide to Molecular Cloning Techniques Methods in Enzymology* volume 152 Academic Press, Inc., San Diego, Calif. (Berger); Sambrook et al., *Molecular Cloning—A Laboratory Manual* (3rd Ed.), Vol. 1-3, Cold Spring Harbor Laboratory, Cold Spring Harbor, N.Y., 2001 ("Sambrook"); and/or *Current Protocols in Molecular Biology*, F. M. Ausubel et al., eds., Current Protocols, a joint venture between Greene Publishing Associates, Inc. and John Wiley & Sons, Inc., (supplemented through 2002) ("Ausubel")). A plethora of kits are also commercially available for the purification of nucleic acids from cells or other samples (see, e.g., EasyPrep™, FlexiPrep™, both from Pharmacia Biotech; StrataClean™, from Stratagene; and, QIAprep™ from Qiagen). Alternately, samples can simply be directly subjected to amplification or detection, e.g., following aliquotting and/or dilution.

Examples of markers for placebo effect susceptibility can include polymorphisms, single nucleotide polymorphisms, haplotypes, presence of one or more nucleic acids in a sample, absence of one or more nucleic acids in a sample, presence of one or more genomic DNA, absence or one or more genomic DNA, presence of one or more mRNA, absence of one or more mRNA, expression levels of one or more mRNAs, presence of one or more proteins, expression levels of one or more proteins, and/or data derived from any of the preceding or combinations thereof. Essentially any number of markers can be detected, using available methods, e.g., using array technologies that provide high density, high throughput marker mapping. Thus, at least about 1, 10, 100, 1,000, 10,000, or even 100,000 or more genetic markers can be tested, simultaneously or in a serial fashion (or combination thereof), for correlation to a placebo effect, in the first and/or second population. Combinations of markers can also be desirably tested, e.g., to identify genetic or expression patterns in populations that are correlated to the placebo effect. For example, comparing the first and second genetic marker can include determining a first haplotype for the first individual or population and determining a second haplotype of the second individual or population, and comparing the first and second haplotypes to identify correlations with one or more placebo effects.

The biological marker to be detected can be any detectable biological component, whether inherited or due to environmental effects or both. Commonly detected markers include genetic markers (e.g., DNA sequence markers present in genomic DNA or expression products thereof) and expression markers (which can reflect genetically coded factors, environmental factors, or both). Where the markers are expression markers, the methods can include determining a first expression profile for the first individual or population (e.g., of one or more expressed markers, e.g., a set of expressed markers) and comparing the first expression profile to a second expression profile for the second individual or population. In this example, correlating the first or second marker can include correlating the first or second expression profile to the placebo effect.

Correlating Markers to Placebo Effect Susceptibility

Correlation of the first or second marker to the placebo effect optionally includes performing one or more statistical tests for correlation. Many statistical tests are known, and most are computer-implemented for ease of analysis. A variety of statistical methods of determining associations/correlations between phenotypic traits and biological markers are known and can be applied to the present invention. For an introduction to the topic, see, Hartl (1981) *A Primer of Population Genetics* Washington University, Saint Louis Sinauer Associates, Inc. Sunderland, Mass. ISBN: 0-087893-271-2. A variety of appropriate statistical models are described in Lynch and Walsh (1998) *Genetics and Analysis of Quantitative Traits*, Sinauer Associates, Inc. Sunderland Mass. ISBN 0-87893-481-2. These models can, for example, provide for correlations between genotypic and phenotypic (e.g., in this case, placebo effect susceptibility) values, characterize the influence of a locus on a phenotype, sort out the relationship between environment and genotype, determine dominance or penetrance of genes, determine maternal and other epigenetic effects, determine principle components in an analysis (via principle component analysis, or PCA), and the like. The references cited in these texts provides considerable further detail on statistical models for correlating markers and phenotype. Further, additional methods for correlating markers to phenotypes (e.g., by performing association studies) are described, for example, in U.S. patent application Ser. No. 10/106,097, filed Mar. 26, 2002; Ser. No. 10/768,788, filed Jan. 30, 2004; Ser. No. 10/786,475, filed Apr. 30, 2003; Ser. No. 10/845,316, filed May 12, 2004; 60/518,107, filed Nov. 6, 2003; and 60/590,534, filed Jul. 22, 2004.

In one such embodiment, markers that are correlated with a phenotypic trait (e.g. exhibition of placebo effect) are identified using regression analysis to process association study data. Such association study data may comprise, for example, information regarding markers carried or expressed by individuals in the study, e.g., genotypes, or levels of expressed RNAs and/or proteins. Linear regression or logistic regression analyses may be used, both of which are well known in the art. Models used with these analyses may incorporate such parameters as age or gender of the subjects being tested, and a measure of their response to a treatment (e.g. placebo). Such a measure may be continuous or may instead be represented by a binary outcome. In some embodiments, an analysis of covariance (ANCOVA) model may be used. The regression analysis models may be used to test each of a set of one or more candidate markers to determine which are likely to be markers that are actually correlated with a placebo effect. Further, statistical significance may be assessed using the q-value approach (Storey et al. (2003) "Statistical significance for genome wide studies", Proc. Natl. Acad. Sci. 100(16):9440-9445), a method based on an assessment of the overall false discovery rate of the experiment, as opposed to controlling the probability of any single false positive result.

In addition to standard statistical methods for determining correlation, other methods that determine correlations by pattern recognition and training, such as the use of genetic algorithms, can be used to determine correlations between markers and phenotypes. To illustrate, neural network approaches can be coupled to genetic algorithm-type programming for heuristic development of a structure-function data space model that determines correlations between genetic information and phenotypic outcomes. For example, NNUGA (Neural Network Using Genetic Algorithms) is an available program (e.g., on the world wide web at cs.b-gu.ac.il/~omri/NNUGA which couples neural networks and genetic algorithms. An introduction to neural networks can be found, e.g., in Kevin Gurney, *An Introduction to Neural Networks*, UCL Press (1999) and on the world wide web at shef.ac.uk/psychology/gurney/notes/index.html. Additional useful neural network references include those noted above in regard to genetic algorithms and, e.g., Bishop, *Neural Networks for Pattern Recognition*, Oxford University Press (1995), and Ripley et al., *Pattern Recognition and Neural Networks*, Cambridge University Press (1995).

Additional references that are useful in understanding data analysis applications to establishing correlations, principle components of an analysis, neural network modeling and the like, include, e.g., Hinchliffe, *Modeling Molecular Structures*, John Wiley and Sons (1996), Gibas and Jambeck, *Bioinformatics Computer Skills*, O'Reilly (2001), Pevzner, *Computational Molecular Biology and Algorithmic Approach*, The MIT Press (2000), Durbin et al., *Biological Sequence Analysis: Probabilistic Models of Proteins and Nucleic Acids*, Cambridge University Press (1998), and Rashidi and Buehler, *Bioinformatic Basics: Applications in Biological Science and Medicine*, CRC Press LLC (2000).

In any case, essentially any statistical test can be applied in a computer implemented model, by standard programming methods, or using any of a variety of "off the shelf" software packages that perform such statistical analyses, including, for example, those noted above and those that are commercially available, e.g., from Partek Incorporated (St. Peters, Mo.; www.partek.com), e.g., that provide software for pattern recognition (e.g., which provide Partek Pro 2000 Pattern Recognition Software) which can be applied to genetic algorithms for multivariate data analysis, interactive visualization, variable selection, neural network & statistical modeling, etc. Relationships can be analyzed, e.g., by Principal Components Analysis (PCA) mapped mapped scatterplots and biplots, Multi-Dimensional Scaling (MDS) Multi-Dimensional Scaling (MDS) mapped scatterplots, star plots, etc.

Placebo effect marker(s), or patterns corresponding thereto, can be used for any of a variety of genetic analyses. For example, once informative markers have been identified, they may be used in a number of different assays for association studies. For example, probes may be designed for micro arrays that interrogate these informative SNPs. Other exemplary assays include, e.g., the Taqman assays and molecular beacon assays, as well as conventional PCR and/or sequencing techniques.

In some embodiments, the marker data is used to perform association studies to show correlation between markers and placebo susceptibility. This can be accomplished by determining marker characteristics in individuals with placebo effect susceptibility (i.e., individuals or populations displaying the phenotype of interest) and comparing the frequency or other characteristics (expression levels, etc.) of the markers in these individuals to the frequency or other characteristics in a control group of individuals. Such marker determinations can be conducted on a genome-wide basis, or can be focused on specific regions of the genome (e.g., haplotypes of interest). In addition to the other embodiments of the methods of the present invention disclosed herein, the methods additionally allow for the "dissection" of a phenotype. That is, a particular placebo susceptibility can result from two or more different genetic bases. For example, a susceptibility phenotype in one individual may be the result of a "defect" (or simply a particular allele—"defect" with respect to a placebo effect susceptibility phenotype is context dependent, e.g., whether the phenotype is desirable or undesirable in the system at issue) in Gene X, while the phenotype in a different individual may be the result of "defects" in Genes Y and Z. Thus, scanning a plurality of markers (e.g., as in whole genome scanning) allows for establishing the correlation of varying genetic bases for similar placebo effect susceptibility phenotypes. Once specific regions of the genome are identified as being associated with a particular phenotype, these regions may be used as drug discovery targets or as diagnostic markers.

As described in the previous paragraph, one method of conducting association studies is to compare the frequency (or expression level) of markers in individuals with a phenotype of interest to the marker frequency in a control group of individuals. In one preferred method, informative SNPs are used to make the SNP haplotype pattern comparison (an "informative SNP" is genetic SNP marker such as a SNP or subset (more than one) of SNPs in a genome or haplotype that tends to distinguish one SNP or genome or haplotype pattern from other SNP patterns). The approach of using informative SNPs has an advantage over other whole genome scanning or genotyping methods known in the art, for instead of reading all 3 billion bases of each individual's genome—or even reading the 3-4 million common SNPs that may be found—only informative SNPs from a sample population need to be detected. Reading these particular, informative SNPs provides sufficient information to allow statistically accurate association data to be extracted from specific experimental populations, as described above.

Thus, in an embodiment of a method of the present invention for determining genetic associations with placebo effect susceptibilities, the frequency of informative SNPs is determined for genomes of a control population that do not display the phenotype. The frequency of informative SNPs is also determined for genomes of a population that do display the phenotype. The informative SNP frequencies are compared. Frequency comparisons can be made, for example, by determining the minor allele frequency (e.g., the number of minor alleles divided by the total number of alleles) at each informative SNP location in each population and comparing these minor allele frequencies. The informative SNPs displaying a difference between the frequency of occurrence in the control versus clinical populations are selected for analysis. Once informative SNPs are selected, the SNP haplotype block(s) that contain the informative SNPs are identified, which in turn identifies a genomic region of interest that is correlated with the phenotype. The genomic regions can be analyzed by genetic or any biological or biochemical methods known in the art e.g., for possible use as drug discovery targets or as diagnostic markers (e.g., to normalize clinical trial information) as described in detail below.

In one such example, an association study to identify SNPs that are correlated with a phenotype may not be undertaken de novo, and may instead comprise combined data from one or more independent studies. Such independent studies may have different durations, criteria for inclusion of subjects, and other variables. The values for each of these variables for each subject tested may be incorporated into the regression models used to analyze each SNP for correlation with the phenotype, as described above. Preferably a common measurement is used to determine response or nonresponse in each of the independent studies, and biological material is available from each subject for screening. Once the biological samples from each subject in the independent studies has been screened for one or more markers, the resultant screening data is combined with the independent study data comprising the response of the individuals to a treatment (e.g. placebo) to determine if any markers screened are correlated with a particular treatment response. For example, if genetic screening reveals that a particular allele of a SNP is present far more often in individuals who experienced a placebo effect, then that allele may be correlated with exhibition of the placebo effect.

Placebo Effects to be Tested For

Placebos are typically classified into two groups, those that are considered "inert" and those that are considered "active." Inert (sometimes called "pure" placebos are substances that are thought to have no pharmacologic effect on the patient. Examples include dummy pills or capsules containing lactose or other sugars, or even chalk, e.g., as typically used for treatment in control groups of clinical trials. Active or "impure" placebos actually do have potential pharmacological effects, though not generally any activity that seems specific for the condition under treatment. Examples include vitamin B12, iron (e.g., for treatments of conditions other than anemia), use of antibiotics to treat viral infections (a popular treatment option, with no clear causal connection between the antibiotic and the viral infection) or even the use of diuretics to treat obesity.

Placebo effects are results obtained by the use of a placebo. Placebo effects include the psychological, physiological or psycho-physiological effect of any medication or procedure, operating through a psychological, rather than a physiological mechanism. The placebo provides a change in a patient's illness (positive or negative) attributable to treatment per se, rather than to a specific pharmacologic or physiologic property of the treatment. A variety of placebo effects have been observed, including clinically significant improvement in angina symptoms (maintained long after "sham" surgery), response to placebos as antidepressants that rivals that of prescription antidepressants, and many others. Placebos may cause adverse side effects. Here the placebo is often called a "nocebo", a word derived from the Latin word "nocere" meaning inflicting harm. Placebo dependence has also been observed (patients have been reported to be addicted to placebos). It has been claimed that the placebo effect can be recognized through a number of distinctive characteristics such as short duration, diminishing effect on repeated doses and no adverse effects. However, this is simply incorrect—the only clear difference between active and placebo treatments seems to be in the degree of the observed effects. A variety of placebo effects are reviewed in Vandana Roy and Tushar Roy (2001) "Placebos: Current Status" *Indian Journal of Pharmacology* 33:396-409.

In general, any of a variety of placebo effects can be tested for, including improvements in a condition or conditions of the first or second individual or population in response to administration of the placebo, and/or a deterioration in a condition of the first or second individual or population in response to administration of the placebo. Placebo effects can also include, e.g., unwanted side effects, e.g., similar to those that may be encountered upon administration of a given drug (e.g., headache, changes in digestive patterns, sleep pattern alterations such as insomnia or increased drowsiness, etc.). The placebo itself can be any of those typically administered to patient, e.g., tablets, suspensions or injections of inert ingredients, e.g., chalk, sugar pills and/or starch pills, or other mock therapies, e.g., fake surgical procedures, fake psychiatric care, or others that have been used, typically as controls, for a putative "real" treatments. Thus, the placebo can comprise one or more inert ingredients, or even one or more active ingredients (e.g., where the activity is expected to be orthogonal to the therapy at issue, as in the case of the use of iron to treat diseases other than anemia, or in the case where the pharmacological effects are diffused, e.g., in the case of vitamin $B_{12}$).

Screening Populations for Placebo Effect Susceptible Members

In a second related set of embodiments, methods of screening an individual or population for susceptibility to a placebo effect are provided. In these methods, a biological sample derived from the individual or population, or data corresponding to the biological sample is analyzed for a presence or absence of one or more biological marker(s) associated with the placebo effect. This determines susceptibility to the placebo effect for the individual or population. Thus, the embodiments noted above provide, e.g., methods of determining whether an association between a marker and a placebo effect exist, while this set of embodiments provides, e.g., a method of screening individuals for a placebo effect correlation with a marker, once such a correlation is determined (e.g., by any method noted above, or any other method). It will be appreciated that the types of markers, types of placebo effects, and types of placebos that are applicable to this method are those noted above.

Any or all of the methods of detecting markers noted above apply to this class of embodiments as well. These include array based marker detection, solution phase marker detection, amplification strategies, and the like. Any available detection method is used to detect markers that to correlate to placebo effect susceptibility. These detection methods can be operated in a high throughput format, e.g., performing a multiplexed analysis of many patient samples simultaneously to detect particular alleles, expression levels, proteins, or the like, that are correlated to placebo effect detection. In general, an appropriate detection step is performed, followed by comparison of the results either to a look up table of markers that are correlated to a placebo effect susceptibility phenotype, or by direct comparison of the detected markers to a control sample known to comprise such markers, or both.

Most typically, this class of embodiments will include determining the presence or absence or expression level of a biological marker in the biological sample (or in data corresponding to the biological sample). For example, the method optionally includes obtaining the biological sample and testing the sample for a genetic or other biological marker.

In any case, once detected, individuals comprising markers correlated to a placebo effect susceptibility phenotype can be selected (for or against) in clinical trials, or can be therapeutically treated with a placebo. Similarly, data from trials can also be normalized to account for the presence of such individuals.

Placebo Therapies

The identification of a biological sample, e.g., from a patient, that shows a correlation to a placebo effect can be useful in designing clinical trials or to detect other experimental drug effects in populations, by accounting for the placebo effect in the relevant clinical trial or experiment. However, the method also provides an avenue for therapy. For example, identification of those members of a population that display a placebo effect provides an avenue for treatment of such members, i.e., by administering one or more therapeutic doses of a placebo to the members of the population that show a placebo effect. As already noted, placebo therapies have been shown to be effective for some patients for treatment of diseases as diverse as heart disease and depression. By selecting those members of the population that are especially susceptible to placebo therapy, the effectiveness of placebo therapy is increased. Such improved targeting of placebo therapies may also be considered to make placebo therapy more ethical. That is, it is not generally considered ethical to treat patients using placebos outside of a clinical trial setting, even though placebo therapy has been shown to be effective in many instances. However, patients that are likely to respond to placebo therapy identified by the methods herein, may be placebo treated in a more ethical fashion.

Designing Clinical Trials to Account for Placebo Effect Suceptibility

As noted, an additional class of methods relates to the ability to design clinical or other trials to account for the placebo effect, taking biological predispositions to the placebo effect into account. Thus, in a first embodiment of this approach, methods of testing a placebo-normalized activity of a putative therapeutic agent are provided. In the methods, the putative therapeutic agent is administered to a first patient population comprising one or more patients. A desired activity of the therapeutic agent is detected. Members that are genetically predisposed to display a placebo effect are identified in the population. Based upon this identification, activity data from the detecting step is normalized to account for the placebo effect, thereby determining the placebo-normalized activity of the putative therapeutic agent.

In a related class of embodiments, alternate methods of testing a placebo-normalized activity of a putative therapeutic agent are provided. In these related methods, members of a first patient population that are genetically predisposed to display a placebo effect are identified. The members are selected (for or against) to provide a placebo-effect normalized patient population. The putative therapeutic agent is administered to the placebo-effect normalized patient population, and, a desired activity of the putative therapeutic agent in the placebo-effect normalized patient population is detected (thereby determining a placebo-normalized activity of the putative therapeutic agent).

In either of these related aspects of the invention, identifying members of the first patient population typically includes identifying at least one biological (e.g., genetic) marker in members of the first population that is correlated to the placebo effect. The types of markers to be detected (and the methods for such detection) and the types of placebo effects to be accounted for include any of those noted above. Further, the placebo-normalized activity of the desired therapeutic agent may be increased or decreased relative to an activity that is not normalized for placebo activity.

Normalizing activity data optionally includes revising estimates of a correlation between the desired activity and administration of the putative therapeutic agent, based upon an expected placebo effect on this correlation. That is, the expected placebo effect normalization takes into account the effect of the population members that are genetically predisposed to display the placebo effect. Such normalizing is optionally performed after obtaining a complete desired activity data set corresponding to the desired activity of the therapeutic agent in the first population, or can be performed during a process of obtaining a desired activity data set corresponding to the desired activity of the therapeutic agent in the first population.

Screening for Placebo Effect Modulators

In addition to the use of placebo effect correlations to design clinical and other experimental trials, the correlations can be used to identify placebo effect-modulatory agents (which can suppress or enhance placebo effects). Such agents can be desirable e.g., as an adjunct to clinical trial design to reduce placebo effects, or as a form of therapy, to enhance the placebo effect as a form of treatment. The methods include, e.g., administering one or more putative placebo effect-modulatory agents to an individual that displays a placebo effect, and determining whether the putative placebo effect-modulatory agent modulates the placebo effect in the individual. This, in turn, determines whether the putative placebo effect-modulatory agent is an actual placebo effect-modulatory agent.

The placebo effect-modulatory agent is optionally a placebo itself, but can also be a therapeutic drug that has an ordinary biological effect. In any case, the actual placebo effect-modulatory agent modulates an activity of a placebo administered to the individual, thereby modulating the placebo effect. In one class of embodiments, this is performed by administering the placebo modulatory agent to individuals that are identified as being either susceptible or non-susceptible to the placebo effect, and determining whether the placebo effect is increased or decreased in the individual. Statistical testing of such changes in the placebo effect across a population are used to determine whether the placebo effect is modulated across a target population.

Systems

As noted to some extent in the preceding discussions of the methods of the invention, the present invention includes system embodiments. These system embodiments generally can include system components for detecting markers. These include, e.g., arrays (e.g., for arraying/detecting marker nucleic acids), thermocyclers (e.g., for amplifying marker nucleic acids, e.g., prior to detection), fluid handlers (for manipulating samples and marker materials), detectors and/or the like. The system components can correlate markers with phenotypes, provide look up tables that include marker-phenotype correlation information, software for operating components of the system, input and output devices (e.g., keyboards, monitors and peripherals for accepting instructions from a user or displaying results to a user), and/or the like.

Systems for Correlating Biological Marker Data to a Biologically-Encoded Placebo Effect In addition to the above methods, the invention provides related systems for practicing the methods (and systems with different functionality as well). In a first class of system embodiments, systems for correlating biological marker data to a biologically-encoded placebo effect are provided. The system includes at least one biological marker data set (e.g., genetic marker data set) corresponding to at least one biological marker that correlates with at least one placebo effect. Typically, such a biological marker data set comprises . . . . The system also typically includes computer-implemented system instructions for correlating the data set to the placebo effect. The biological marker data set can be embodied in a computer or in computer readable media (CD-ROM, hard drive, diskette, tape, etc.).

Systems for Identifying a Genetic Basis for the Placebo Effect

Systems for identifying a genetic basis for a placebo effect are also provided, e.g., for practicing the methods noted above. The systems include at least one genetic marker data set corresponding to at least a first genetic marker and either the same marker or an additional genetic marker for a second individual or population of individuals. Computer-implemented system instructions compare the first genetic marker and the second genetic marker and correlate the first or second marker to the placebo effect, thereby identifying a genetic basis for the placebo effect. Any of the various statistical models noted above can be implemented by computer in this embodiment.

Systems for Screening an Individual or Population for Susceptibility to a Placebo Effect Similarly, systems for screening an individual or population for susceptibility to a placebo effect are provided. The systems include, e.g., data corresponding to one or more test biological markers (e.g., genetic markers) in a biological sample derived from an individual or population and a look up table corresponding to one or more susceptibility markers. Computer-implemented system instructions compare the test genetic markers to the susceptibility markers, thereby determining whether the individuals comprise one or more test biological markers associated with the placebo effect.

For example, the system can include a look up table corresponding to one or more placebo effect susceptibility markers (e.g., biological markers, e.g., genetic markers), where the computer implemented system instructions compare the biological marker data set to the look up table to determine whether the at least one biological marker correlates with one or more entries in the look up table.

Optionally, any of the above systems can include a selection module that selects for or against an individual or population based upon whether the individual comprises the one or more susceptibility markers. Similarly, the systems can include a data normalization module that comprises system instructions that normalize one or more activity data sets for the placebo effect.

Systems for Determining a Placebo-Normalized Activity of a Putative Therapeutic Agent.

In an additional aspect, the invention provides a system for determining a placebo-normalized activity of a putative therapeutic agent. The system includes activity data corresponding to a desired activity of a putative therapeutic agent in a first patient population comprising one or more patients and placebo effect data corresponding to population members of the first population that are biologically (e.g., genetically) predisposed to display a placebo effect. Computer-implemented system instructions provide a normalized data set by adding or subtracting values from the activity data, based upon the placebo effect data.

Generally Applicable System Components

Any of the above systems optionally include additional system components for interfacing with a user. For example, the systems can include a user viewable display for viewing an output of the computer-implemented system instructions, user input devices (e.g., keyboards or pointing devices such as a mouse) for inputting user commands and activating the system, etc. Typically, the system of interest includes a computer, wherein the various computer-implemented system instructions are embodied in computer software, e.g., stored on computer readable media.

Any of the above systems can include a data acquisition module for detecting one or more detectable genetic marker (e.g., one or more arrays comprising one or more biomolecular probes, detectors, fluid handlers, or the like). The biomolecular probes of such a data acquisition module can include any that are appropriate for detecting the biological marker, e.g., oligonucleotide probes, proteins aptamers, antibodies, etc. These can include sample handlers (e.g., fluid handlers), robotics, microfluidic systems, nucleic acid or protein purification modules, arrays (e.g., nucleic acid arrays), detectors, thermocyclers or combinations thereof, e.g., for acquiring samples, diluting or aliquoting samples, purifying marker materials (e.g., nucleic acids or proteins), amplifying marker nucleic acids, detecting amplified marker nucleic acids, and the like.

For example, automated device that can be incorporated into the systems herein have been used to assess a variety of biological phenomena, including, e.g., expression levels of genes in response to selected stimuli (Service (1998) "Microchips Arrays Put DNA on the Spot" *Science* 282: 396-399), high throughput DNA genotyping (Zhang et al. (1999) "Automated and Integrated System for High-Throughput DNA Genotyping Directly from Blood" *Anal. Chem.* 71:1138-1145) and many others. Similarly, integrated systems for performing mixing experiments, DNA amplification, DNA sequencing and the like are also available. See, e.g., Service (1998) "Coming Soon: the Pocket DNA Sequencer" *Science* 282:399-401. A variety of automated system components are available from the Zymark Corporation (Zymark Center, Hopkinton, Mass.), which utilize various Zymate systems (see also, www.zymark.com), which typically include, e.g., robotics and fluid handling modules. Similarly, the common ORCA® robot, which is used in a variety of laboratory systems, e.g., for microtiter tray manipulation, is also commercially available, e.g., from Beckman Coulter, Inc. (Fullerton, Calif.). Similarly, commercially available microfluidic systems that can be used as system components in the present invention include those from Hewlett-Packard/Agilent Technologies (e.g., the HP2100 bioanalyzer) and the Caliper High Throughput Screening System (see, e.g., http://www.calipertech.com/products/index.htm). The Caliper High Throughput Screening System provides an interface between standard library formats and chip technologies (see, e.g., http://www.calipertech.com). Furthermore, the patent and technical literature includes examples of microfluidic systems which can interface directly with microwell plates for fluid handling.

Any of a variety of liquid handling and array configurations can be used in the systems herein. One common format for use in the systems herein is a microtiter plate, in which the array or liquid handler is includes a microtiter tray. Such trays are commercially available and can be ordered in a variety of well sizes and numbers of wells per tray, as well as with any of a variety of functionalized surfaces for binding of assay or array components. Common trays include the ubiquitous 96 well plate, with 384 and 1536 well plates also in common use. Samples can be processed in such trays, with all of the processing steps being performed in the trays.

In addition to liquid phase arrays, components can be stored in or analyzed on solid phase arrays. These arrays fix materials in a spatially accessible pattern (e.g., a grid of rows and columns) onto a solid substrate such as a membrane (e.g., nylon or nitrocellulose), a polymer or ceramic surface, a glass or modified silica surface, a metal surface, or the like. Components can be accessed, e.g., by hybridization, by local rehydration (e.g., using a pipette or other fluid handling element) and fluidic transfer, or by scraping the array or cutting out sites of interest on the array.

Kits

Any of the above systems can be packaged as kits, e.g., comprising one or more system components and instructional materials for practicing one or more of the methods herein, packaging materials, or the like.

OTHER EMBODIMENTS

Although the above discussion has presented the present invention according to specific processes and apparatus, the present invention has a much broader range of applicability. For example, the present invention is not limited to SNP pattern discovery, though this is an example embodiment noted in some detail above. Other areas of biological research and pattern recognition generally can profit from the methods of this invention. Of course, one of ordinary skill in the art would recognize other variations, modifications, and alternatives.

While the foregoing invention has been described in some detail for purposes of clarity and understanding, it will be clear to one skilled in the art from a reading of this disclosure that various changes in form and detail can be made without departing from the true scope of the invention. For example, all the techniques and systems/devices/kits/apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of performing an association study to identify a correlation between one or more genetic markers and a placebo effect, the method comprising:
   determining a first frequency of the one or more markers for a first population;
   determining a second frequency of the one or more markers in a second population, wherein the first population differentially exhibits the placebo effect as compared to the second population; and,
   comparing the first frequency and the second frequency, wherein a difference between the first frequency and the second frequency indicates a correlation between the one or more genetic markers and the placebo effect.

2. A method of identifying whether an individual is susceptible or predisposed to a placebo effect, the method comprising:
   obtaining a biological sample from the individual; and,
   detecting whether the one or more genetic markers of claim 1 are present in the sample, wherein presence of the one or more biological markers indicates the individual is susceptible to the placebo effect.

3. The method of claim 1, wherein the placebo effect is selected from the group of effects consisting of: an improvement in a condition in the first or second population in response to administration of a placebo, and a deterioration in a condition in the first or second population in response to administration of the placebo.

4. The method of claim 3, wherein the placebo is selected from the group consisting of a suspension, a tablet, an intravenous injection, and a surgical procedure.

5. The method of claim 3, wherein the placebo comprises one or more inert ingredients.

6. The method of claim 3, wherein the placebo comprises an active placebo.

7. The method of claim 1, wherein the one or more genetic markers comprise one or more haplotypes.

8. The method of claim 1, wherein the one or more genetic markers are allelic variants of a genetic locus.

9. The method of claim 1, comprising comparing the first frequency of at least 10 genetic markers in the first population to the second frequency of the at least 10 genetic markers in the second population.

10. The method of claim 1, comprising comparing the first frequency of at least 100 genetic markers in the first population to the second frequency of the at least 100 genetic markers in the second population.

11. The method of claim 1, comprising comparing the first frequency of at least 1000 genetic markers in the first population to the second frequency of the at least 1000 genetic markers in the second population.

12. The method of claim 1, wherein the one or more genetic markers comprise one or more of: an allele of a polymorphism, an allele of a single nucleotide polymorphism, presence of one or more nucleic acids, absence of one or more nucleic acids, presence of one or more genomic DNAs, absence or one or more genomic DNAs, presence of one or more mRNAs, absence of one or more mRNAs, an expression level of one or more mRNAs, presence of one or more proteins, or an expression level of one or more proteins.

13. The method of claim 1, wherein determining the first frequency comprises determining a first haplotype for the first population, and determining the second frequency comprises determining a second haplotype of the second population, and comparing the first and second frequency comprises comparing the first and second haplotypes.

* * * * *